United States Patent [19]

Schewe et al.

[11] Patent Number: 4,816,487

[45] Date of Patent: * Mar. 28, 1989

[54] 1-(2-HYDROXYARYL)-ALKANE-1-ON-OXIMES-PROCEDURE OF PREPARATION AND USE IN PHARMACEUTICALS

[75] Inventors: Tankred Schewe; Hartmut Kuehn, both of Berlin; Joerg Beger, Freiberg; Grupe, Renate; Rapoport, Samuel M., both of Berlin; Hans-Joachim Binte, deceased, late of Freiberg, by Ingrid Binte, administrator; Juergen Slapke, Berlin, all of German Democratic Rep.

[73] Assignee: Humboldt-Universitaet zu Berlin, Berlin, German Democratic Rep.

[*] Notice: The portion of the term of this patent subsequent to Feb. 28, 2005 has been disclaimed.

[21] Appl. No.: 711,879

[22] Filed: Mar. 14, 1985

[51] Int. Cl.$^4$ .............................................. A61K 31/15
[52] U.S. Cl. ...................................... 514/640; 564/254; 564/255; 564/256; 564/265
[58] Field of Search ................ 564/254, 255, 265, 253; 514/640

[56] References Cited

U.S. PATENT DOCUMENTS

| | | | |
|---|---|---|---|
| 3,579,556 | 5/1971 | Briggs et al. | 564/265 |
| 4,141,995 | 2/1979 | Saunders et al. | 514/640 |
| 4,678,810 | 7/1987 | Danree | 514/640 |

FOREIGN PATENT DOCUMENTS

| | | | |
|---|---|---|---|
| 2305694 | 8/1973 | Fed. Rep. of Germany | 514/640 |
| 2342878 | 2/1974 | Fed. Rep. of Germany | 514/640 |
| 2461039 | 6/1976 | Fed. Rep. of Germany | 514/640 |
| 2407200 | 8/1975 | German Democratic Rep. | 564/265 |
| 1441174 | 6/1976 | United Kingdom | 514/640 |

OTHER PUBLICATIONS

Krauch, Helmut et al, *Organic Name Reactions* (1964) John Wiley & Sons, Publ. At p. 491.
Synthesis vol. 1 (Jan. 1982) pp. 68–69; Georg Thieme Verlag, Stuttgart, New York; Table 1, Example 28.

*Primary Examiner*—James H. Reamer
*Attorney, Agent, or Firm*—Jordan and Hamburg

[57] ABSTRACT

New 1-(2-hydroxylaryl)-alkane-1-on-oximes, procedure for their preparation, and their applicability to pharmaceutical preparations. One purpose is to develop 1-(2-hydroxyaryl)-alkane-1-on-oximes with desirable pharmacological properties. The new compounds of Formula I

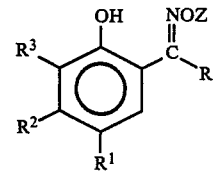

are characterised by pharmacologically valuable properties, in particular by anti-asthmatic, anti-anaphylactic, antiphlogistic, antihypertensive, spasmolytic, antirheumatic, and antithrombotic, potentials and are applicable in human and veterinary medicine to therapy of asthma bronchiale and other allergic diseases, various kinds of inflammatory and rheumatic diseases, and thrombosis.

21 Claims, No Drawings

1-(2-HYDROXYARYL)-ALKANE-1-ON-OXIMES-PROCEDURE OF PREPARATION AND USE IN PHARMACEUTICALS

BACKGROUND OF THE INVENTION AND PRIOR ART STATEMENT

This invention relates partially to new 1-(2-hydroxyaryl)-alkane-1-on-oximes, processes for their preparation, and their applicability to pharmaceutical preparations. The compounds in their own right and, consequently, the pharmaceutical products in which they are contained are characterised by useful pharmacological, especially anti-asthmatic, anti-anaphylactic, antiphlogistic, antihypertensive, spasmolytic, anti-rheumatic, and antithrombotic properties and are applicable in human and veterinary medicine to the treatment of asthma bronchiale and other allergic diseases, various inflammatory and rheumatic diseases, and thrombosis.

Processes for the preparation of ketoximes have been well known, as a matter of fact, and can be found in any manual on organic synthesis (cf. Weygand-Hilgetag, Organisch-Chemische Experimentierkunst). Several methods have been described in the literature for conversion of 1-aryl-alkane-1-ones with hydroxylamine-hydrochloride to oximes. Yet, in many instances conditions and rates of reaction, types of bases used, and other factors had not been optimally chosen in dependence on the parent ketone and its structure. The 1-(2-hydroxyphenyl)-alkane-1-on-oximes, within the framework of 1-aryl-alkane-1-on-oximes, are, typically, used as metal reagents in metal analysis and as selective metal extraction agents in liquid-liquid extraction (BRD-OS-2342878). 5-iso-nonyl-2-hydroxyacetophenone-oxime (SME 529 of Shell Chemicals) has assumed technical importance to the production of copper (Extr. Metal Copper Int. Symp. 1976, 1039). No information whatsoever has been recordable regarding a pharmaceutical application of these compounds in human or veterinary medicine.

SUMMARY OF THE INVENTION

The invention has been made for the object of making available pharmaceutical preparations with pharmacologically desirable properties, with particular emphasis being laid on anti-asthmatic, anti-anaphylactic, anti-phlogistic, anti-rheumatic, antihypertensive, spasmolytic, and antithrombotic parameters.

The invention has been made, with the further object of developing new 1-(2-hydroxyaryl)-alkane-1-on-oximes with anti-asthmatic and other pharmacologically desirable properties based on inhibition of lipoxygenase as well as to devising methods for their preparation and to using them as medicaments.

These and other objects and advantages of the present invention will become evident from the description which follows.

It was, surprisingly, found that pharmacologically valuable properties, especially anti-asthmatic, anti-allergic, anti-phlogistic, antirheumatic, antihypertensive, spasmolytic, and antithrombotic characteristics, were exhibited by 1-(2-hydroxyaryl)-alkane-1-on-oximes of the general formula given below and that these oximes proved suitable for use as effective components in pharmaceutical preparations:

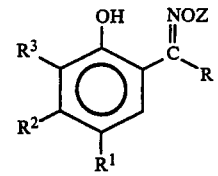

where:
R $C_{1-18}$-alkyl or aralkyl
$R^1$ and $R^3$ hydrogen, $C_{1-12}$-alkyl or chlorine
$R^2$ hydrogen, $C_{1-12}$-alkyl or $OR^4$, with $R^4$ standing for $C_{1-18}$-alkyl, $C_{3-8}$-cycloalkyl or aralkyl
Z hydrogen, $C_{1-12}$-alkyl, $COR^5$ or $CONHR^5$, with $R^5$ standing for aromatic or aliphatic residues.

Another finding made was that a process for the preparation of Formula I compounds should be characterised by conversion under Friedel-Crafts or similar conditions of acylation of an aliphatic carbonic acid, $C_nH_{2n+1}COOH$, or a suitable derivative of the latter, preferably a carboxylic acid chloride, with a substituted phenol. Should an additional hydroxyl group be contained in the resulting ketone, it is likely to be etherified with an alkylation agent, such as alkylhalogenide, aralkylbromide or cycloalkylbromide or cycloalkylchloride, with alkylbromide being preferably involved.

The ketone will then be converted to an oxime in the well-known way, with hydroxylamine-hydrochloride or with another appropriate hydroxylamine salt in basic medium. Inorganic or organic bases may be used, in this context, for example, sodium hydroxide, potassium hydroxide, calcium hydroxide, sodium carbonate, potassium carbonate, sodium bicarbonate, sodium acetate, potassium acetate, sodium formate, pyridine, piperidine, morpholine, N-methylpiperazine, diethanolamine, and others. Etherification and oximation take place in organic solvents, with etherification being conducted primarily in acetone or lower aliphatic alcohols, with one of the above basic substances added, potassium carbonate or sodium hydroxide, being preferred. Oximation is likely to occur in lower aliphatic alcohols or glycols, acetonitrile, and dioxan, but primarily in ethanol, or in mixtures of these with water. Reaction temperatures are between 50° C. and 130° C. Rates of reaction are between 15 and 30 hours for alkylation or between 15 minutes and three hours for oximation.

New compounds, so far not described in the literature were obtained from the above process. They are characterised below with regard to elementary analysis, melting pont, and properties in the infrared spectrum and are summarised in Table 1.

Unexpected findings suggested that the compounds of general Formula I, which are subject of this invention, exhibited unambiguous anti-asthmatic, anti-allergic, and anti-anaphylactic effects in in-vitro and in-vivo animal experiments.

These pharmacological properties were largely verified by measuring methods which were, basically, known from the literature. They were, however, applied in a modified form. Points of application for verification included trachea isolated from guinea pig, lung strip isolated from guinea pig, such as arachidonic-acid-induced contraction of isolated lung strip (cf. Example 16), isolated pulmonary artery (cf. Example 18), and specific-allergically induced bronchoconstriction of guinea pig which had been ovalbumin-sensitised, anaesthetised, and artificially ventilated ("guinea pig asthma"

or "anaphylaxis of guinea pig") (cf. Example 17) [M. W. Drazen et al., J. Clin. Invest. 63, 1 (1979); M. W. Schneider and J. M. Drazen, Amer. Rev. Resp. Dis. 121, 835 (1980); S. S. Yen and W. Kreutner, Agents Actions 10, 174 (1980); S. S. Yen, Prostaglandins 22, 183 (1981); Adcock, J. J.; Garland, L. G.; Brit. J. Pharmacol. 69, 167 (1980); W. Diamantis, J. L. Melton; D. Sofia et al., Europ. J. Pharmacol. 56, 407 (1979); P. Anderson, Brit. J. Pharmacol. 77, 301 (1982)].

The compounds of general Formula I, according to this invention, have proved to result in complete inhibition of ovalbumin-induced asthma reaction in ovalbumin-sensitised guinea pig. It was, remarkably, observed that all control animals died of apnoea after one single intraperitoneal application of ovalbumin (40 μg/kg body weight), following protracted and extremely severe asthmatic reaction (anaphylactic shock?). On the other hand, even three successive ovalbumin injections of 40 μg were tolerated without any sign of bronchoconstriction by animals which had been pretreated, using one of the substances referred to in this invention (5-methyl-2-hydroxyl-laurophenone-oxime).

/R. Andersson, Brit. J. Pharmacol. 77, 301 (1982)/. The conclusion was, therefore, drawn that the comounds of general Formula I, according to this invention, should, as well, have clearly pronounced antiphlogistic properties. That conclusion was positively verified in vivo by an appropriate inflammatory model in the context of an animal experiment, using carragheenin—induced oedema of rat's paw. The experimental model was handled according to a method proposed by Winter and co-workers /C. A. Winter, E. A. Risley, and G. W. Nuss, Proc. Soc. Exp. Biol. Med. 111, 544 (1962)/ (cf. Example 19).

Inhibition of lipoxygenase was identified as the molecular point of attack for the pharmacological effects of the compounds according to this invention. The metabolites of arachidonic acid, enzymatically formed by lipoxygenase, are known to be involved in the pathogenesis of inflammatory and allergic processes /cf. E. J. Goetzl, Immunology, 40, 709 (1980); Ford-Hutchinson et al., J. Pharm. Pharmacol., 32, 517 (1980); B. Samuelsson, Trends in Pharmacol. Sci., May 1980, 227; Borgeat et al., J. Med. Chem. 24, 121 (1981)/.

TABLE 1

| New 1-(2-hydroxylaryl)-alkano-1-on-oximes | | | | |
|---|---|---|---|---|
| Compound | $F_p$ (°C.) | $\nu$max (OH) | (KBr; cm$^{-1}$) (C=N) | (N—O) |
| 4-methyl-2-hydroxy-caprophenone-oxime | 45 | 3390 | 1630 | 980 |
| 5-methyl-2-hydroxy-caprophenone-oxime | 83–85 | 3380 | 1628 | 982 |
| 5-methyl-2-hydroxy-caprophenone-(N—phenylcarbamoyl)-oxime | 117–120 117–120 | | | |
| 5-methyl-2-hydroxy-laurophenone-oxime | 93 | 3380 | 1626 | 972 |
| 3-chloro-2-hydroxy-caprophenone-oxime | 102–103 | 3390 | 1638 | 975 |
| 4-pentoxy-2-hydroxy-acetophenone-oxime | 66–67 | 3420 | 1640 | 980 |
| 4-decyloxy-2-hydroxy-acetophenone-oxime | 69–70 | 3425 3350 | 1628s* | 975 |
| 4-benzyloxy-2-hydroxy-acetophenone-oxime | 143 | 3360 | 1630 | 962 |
| 4-decyloxy-2-hydroxy-propiophenone-oxime | 58–59 | 3390 | 1632 | 990 |
| 4-butoxy-5-n-hexyl-2-hydroxy-acetophenone-oxime | 62 | 3410 | 1640s* | 970 |
| 4-pentoxy-2-hydroxy-caprophenone-oxime | 80 | 3360 | 1640 | 985 |
| 4-decyloxy-2-hydroxy-caprophenone-oxime | 57 | 3430 | 1648 | 980 |
| 4-octyloxy-2-hydroxy-laurophenone-oxime | 60–63 | 3430 | 1640s* | 985 |
| 4-cyclohexyloxy-2-hydroxy-propiophenone-oxime | 65–69 | 3440 | 1640 | 988 |
| 5-chloro-2-hydroxy-caprophenone-oxime | 100 | 3385 3335s* | 1640 | 990 |
| 5-chloro-2-hydroxy-laurophenone-oxime | 96 | 3395 | 1640 | 972 |
| 5-chloro-2-hydroxy-laurophenone-oxime | 97 | 3380 | 1635 | 970 |
| 4-butoxy-2-hydroxy-acetopheone-oxime | 87 | 3422 | 1640 | 988 |
| 4-dodecyloxy-2-hydroxy-propiophenone-oxime | 63 | 3395 | 1635 | 988 |
| Compound | $F_p$ (°C.) | $\lambda$max (OH) | (KBr; cm$^{-1}$) (C=N) | (N—O) |
| 4-hexadecyloxy-2-hydroxy-acetophenone-oxime | 86–87 | 3425 3350 | 1625 | 973 |
| 4-octadecyloxy-2-hydroxy-acetophenone-oxime | 90 | 3410 3360s* | 1627 | 980 |
| 4-decyloxy-2-hydroxy-laurophenone-oxime | 64–69 | 3430 | 1648 | 987 |

*s = shoulder

The above recorded effect on allergic asthma was comparable to that obtainable from Ketotifen, a modern anti-asthmatic, yet, with a molecular mechanism of action which differs from that of the compounds according to this invention (see below). The compounds according to this invention are superior to Ketotifen by virture of their much wider range of indications, in other words, their effectiveness also on non-allergic forms of asthma bronchiale. Evidence to antihypertensive and spasmolytic effects has been adduced (Example 18) by the inhibition of arachidonic-acid-induced contraction of pulmonary artery isolated from rabbit.

This method is an adequate model of asthma bronchiale forms in experimental animals with involvement of IgE-dependent and IgG-dependent allergic reactions Persuasive evidence to inhibition of lipoxygenase was produced by a suitable animal lipoxygenase which had been isolated from rabbit reticulocytes, using a method by Rapoport and coworkers /S. M. Rapoport et al., Eur. J. Biochem. 96, 545 (1979)/. A final concentration of 1 mM of most of the compounds, according to this invention, produced inhibition of 90 percent or more (cf. Example 20). Significant inhibition was even recordable from a final concentration of 0.1 mM of some of the compounds, according to this invention. Substance concentrations were varied to determine the titration curves of inhibition and from these the half-inhibition concentrations ($I_{50}$-values). A half-inhibition concentration of 7 μM was established for 5-methyl-2- hydroxy-laurophenone-oxime, an oxime of high anti-asthmatic effectiveness. However, the fact that this, as many of the other compounds referred to in this invention, failed when in-vitro testing was applied to such concentrations on account of their limited solubility in water—visible from unambiguous clouding of the sample—seemed to suggest that in reality the $I_{50}$-values were very much below the above figure. The suitability of lipoxygenase from rabbit reticulocytes as a model to circumscribe the molecular-pharmacological point of action of the compounds, according to this invention, was confirmed when the same enzyme was inhibited with high effectiveness by other lipoxygenase inhibitors known from the literature, among them 3-amino-1-(3-trifluoromethylphenyl)-pyrazoline, 5,8,11,14-eicosa-tetraynoic acid, 5,8,11-eicosatriynoic acid, nordihydroguaiaretic acid, propylgallate, 4-nitrocatechol, and 3-tert.-butyl-4-hydroxy-anisol However, the level of anti-asthmatic effectiveness produced by the compounds of this invention has not been reached by any of the the lipoxygenase inhibitors known in the past. The compounds, according to this invention, have proved to inhibit also all lipoxygenases studied after isolation from plants, such as soybean lipoxygenase-1 (cf. Example 20) and lipoxygenase resulting from pea. These together with additional studies have supported the conclusion that the compounds referred to in this invention are universal inhibitors of lipoxygenases, irrespective of their origin and specific location, and, consequently, exhibit a number of desirable pharmacological properties. Another observation was of particular interest, in this context: Cyclo-oxygenase, another important enzyme of the arachidonic acid cascade and isolated from seminal vesicles of cattle by a method by F. J. G. van der Ouderaa and M. Buytenhek /Methods in Enzymology 86, 60 (1982)/, was not remarkably inhibited up to a final concentration of 1 mM. Hence, the compounds referred to in this invention are superior in this respect to many antiphlogistics known in the past either for their exclusive inhibitory action on cyclooxygenase (e.g. acetylsalicylic acid, indomethacin, etc.) or for inhibiting both lipoxygenase and cyclo-oxygenase (e.g. phenidone), aspects which resulted in undesirable pharmacological side-effects (e.g. ulcerogenic, gastrotoxic, and pro-asthmatic effects of acetylsalicylic acid).

Since inhibition of lipoxygenase was identified as molecular point of attack of these new medicaments, studies were conducted also into their action upon thrombocyte aggregation. The substantive role played by the lipoxygenase route in the irreversibility of thrombocyte aggregation is well established at present/C. E. Dutilh et al., Prostaglandins and Medicine 6, 111 (1981)/. A key role in the pathogenesis of thrombotic diseases is attributed to irreversibility of thrombocyte aggregation. Hence, it is an extremely important result that, depending on experimental conditions, the compounds referred to in this invention are capable of complete inhibition of thrombocyte aggregation or of rendering it reversible (cf. Example 21). In the experiments conducted for this invention, thrombocyte aggregation was triggered off either by arachidonic acid or by the platelet activation factor (PAF-acether).

Hence, evidence to anti-asthmatic, anti-allergic, anti-thrombotic, and anti-inflammatory effects has been produced by the above experiments on the basis of suitable biological models.

The following indications in human and veterinary medicine may be suggested as examples:

1. All forms of asthma bronchiale, including infectious asthma bronchiale (intrinsic asthma), exogenous allergic asthma bronchiale (extrinsic asthma), Types I, II, and IV according to Coombs and Gell /R. A. Coombs and P. G. H. Gell: The classification of allergic reactions responsible for clinical hypersensitivity and disease. In: Clinical aspects of immunology, ed. by P. G. H. Gell and R. R. A. Coombs, p. 575, Blackwell Scientific Publications, Oxford, 1968/, analgetic-induced asthma bronchiale (aspirin-induced asthma), stress-induced asthma bronchiale (exercise-induced asthma), cold-induced asthma, irritative asthma bronchiale, and psychogenic asthma bronchiale.

2. Asthmoid bronchitis and obstructive pulmonary emphysema as well as all conditions of bronchoconstriction which may develop as accompanying symptoms of other diseases or side-effects of medication, including anaesthetic complications or bronchospasm following applicaton of beta-adrenergic blocker substances.

3. The following allergic diseases in a wider context:
Atopic dermatitis;
Allergic rhinitis (seasonal, perennial, and vasomotor rhinitis);
Angio-oedema;
Contact dermatitis (contact eczema);
Allergic diseases of the gastro-intestinal tract;
Allertic conjunctivitis.

4. All forms of thrombosis (thrombophlebitis), including prophylaxis and therapy in the context of the following conditions:
Chronic ischaemic heart disease;
After-treatment of myocardial infarction;
Chronic recurrent thrombosis;
Chronic thrombophlebitis.

5. Use as non-steroid antiphlogistics, with compounds of general Formula I being primarily indicated in cases of those inflammatory processes in which conventional antiphlogistics fail to produce sufficient therapeutic action for their points of attack being outside lipoxygenase (e.g. acetylsalicylic acid, salicylate, etc.), with effective applicability being particularly claimed to purulent inflammations as well as to rheumatic and arthritic diseases.

6. All forms of arterial hypertension, with particular emphasis on pulmonary hypertension (in pulmonary circulation).

7. Spastic conditions of unstriated muscles of differentiated pathogenesis, with some emphasis being laid on certain sections of digestive and urogenital tracts and musculature of blood vessels.

Anti-atherosclerotic, gastroprotective, and antimetastatic effects are also claimed for the compounds of Formula I, according to this invention, as reference can be made to other literature sources on established pharmacological effects of lipoxygenase inhibitors.

The compounds of general Formula I are shown to be suitable active principles for oral, perlingual, rectal, parenteral, intravenous, percutaneous, and aerosolic medicaments therapeutically applicable to various forms of asthma bronchiale, thrombosis as well as of rheumatic, arthritic, and other inflammatory diseases.

The following compounds are separately mentioned for their outstanding pharmacological properties:
5-methyl-2-hydroxy-laurophenone-oxime;
4-methyl-2-hydroxy-caprophenone-oxime;
5-methyl-2-hydroxy-caprophenone-oxime;
4-decyloxy-2-hydroxy-acetophenone-oxime;

4-decyloxy-2-hydroxy-propiophenone-oxime;
4-benzyloxy-2-hydroxy-acetophenone-oxime;
4-decyloxy-2-hydroxy-caprophenone-oxime;
4-hexyloxy-2-hydroxy-acetophenone-oxime;
4-pentoxy-2-hydroxy-acetophenone-oxime;
4-pentoxy-2-hydroxy-caprophenone-oxime;
4-butoxy-5-n-hexyl-2-hydroxy-acetophenone-oxime;
5-methyl-2-hydroxy-caprophenone-(N-phenyl-carbomyl)-oxime.

Included in this invention are pharmaceutical preparations which, in addition to non-toxic, inert pharmaceutically useful carrier substances, contain one or several active principles, in accordance with this invention, or which consist of one or more of such active principles.

Non-toxic, inert, and pharmaceutically suitable carrier substances are meant to be solid, semi-solid or liquid diluents, fillers, and formulation adjuvants of all kinds.

Let preferred pharmaceutical preparations include tablets, lozenges, capsules, pills, granulates, syrups, suppositories, solutions, suspensions, emulsions, pastes, ointments, jellies, creams, lotions, powders, sprays, and aerosols.

Tablets, lozenges, capsules, pills, and granulates can contain one or more active substances in addition to common carrier substances, for example, (a) fillers and extenders, such as starch, lactose, sucrose, glucose, mannitol, and silicic acid; (b) binders, such as carboxymethylcellulose, alginates, gelatin, polyvinylpyrrolidone; /(c)/ moisturisers, such as glycerol; (d) breaking agents, such as agar-agar, calcium carbonate, and sodium bicarbonate; (e) solution retarders, such as paraffin; (f) resorption accelerators, such as quaternary ammonium compounds; (g) wetting agents, such as cetyl alcohol and glycerol monostearate; (h) adsorbents, such as kaolin and bentonite; (i) lubricants, such as talcum, calcium stereate, magnesium stereate, and sodium lauryl sulphate as well as solid polyethylene glycols or mixtures of the substances given from (a) to (i).

Tablets, lozenges, pills, and granulates may be surrounded by commonly used coats, some of these containing opalescent agents, or composed to the effect that they release one or all active substances in them solely or preferably into a certain region of the intestinal tract, perhaps, in a retarded fashion, as the case may be. Polymer substances and waxes might be used, in this context, as embedding compounds.

One or several active substances may, as well, be present in microcapsulated form together with one or more of the above carrier substances.

Suppositories may contain, in addition to active substances, one or more of the commonly used carrier substances, soluble or insoluble in water, such as polyethylene glycols, fats, including cocoa fat, and higher esters, such as $C_{14}$ alcohol with $C_{16}$ fatty acid, or mixtures of these substances.

Ointments, pastes, creams, and gels may contain in them, in addition to active substances, commonly used carrier substances, such as animal or vegetable fats, waxes, paraffins (e.g. crude fractions), starch, tragacanth, cellulose derivatives, polyethylene glycols, silicones, bentonite, talcum, silicic acid, zinc oxide or mixtures of them.

Commonly used carrier substances may be contained, in addition to active substances also in sprays and powders, such as lactose, talcum, silicic acid, aluminium hydroxide, calcium silicate, polyamide powder or mixtures of these. Apart from these, sprays may additionally contain commonly used blowing agents, such as chlorofluorocarbons.

Solutions and emulsions may contain, in addition to active substances, commonly used carrier substances, such as non-toxic organic solvents, solutisers, and emulsifiers, for example, water, dimethyl sulphoxide, ethyl alcohol, isopropyl alcohol, methyl glycol, ethyl carbonate, ethyl acetate, benzyl alcohol, benzyl benzoate, propylene glycol, 1.3-butylene glycol, dimethyl formamide, oils, mainly cottonseed oil, peanut oil, cashew oil, maize oil, olive oil, castor oil, and sesame oil, glycerol, glycerol formate, tetrahyddrofurfuryl alcohol, polyethylene glycols, and fatty acid ester of sorbitol or mixtures of these substances.

Solutions and emulsions may be used also in sterile and haemato-isotonic form for parenteral application. Suspensions may contain, in addition to active substances, commonly used carrier substances, such as liquid diluents, including water dimethyl sulphoxide, ethyl alcohol, propylene glyco, suspending agents, among them ethoxylated isostearyl alcohols, polyoxyethylene sorbitol esters, sorbitane esters, microcrystalline cellulose, aluminium metahydroxide, bentonite, agar-agar, and tragacanth or mixtures of these substances.

Dispersants, too, may be used for formulations, including lignin, spent sulphite liquor, methyl cellulose, starch, and polyvinyl pyrrolidone.

The above forms of formulation may contain also colouring agents, preservatives, odour improvers, and flavour enhancers, such as peppermint oil, eucalyptus oil, and sweeteners, for example, saccharin.

The therapeutically active compounds in the above pharmaceutical preparations should be present in concentrations between 0.1 and 99.5 weight percent relative to the overall mixture, preferrentially in approximate concentrations between 0.5 and 90 weight percent, in other words, in amounts sufficient to accomplish the dosage spectrum claimed.

Pharmaceutically active substances, in addition to those referred to in this invention, may be contained in the above pharmaceutical preparations, among them antihistaminics and cyclo-oxygenase inhibitors.

The above pharmaceutical preparations are made in the usual way by established methods, for example by mixing of active and carrier substances.

Application of the active principles and pharmaceutical preparations, containing one or more of these active principles, to prophylaxis, improvement, and/or healing of the diseases listed earlier in human and veterinary medicine is another object of this invention.

The active principles or pharmaceutical preparations can be applied locally, orally, parenterally, intraperitoneally, and/or rectally, preferably by the oral route, and in the form of aerosol.

It has been, generally, found to be a good practice to administer the active principles, according to this invention, in approximate overall quantities between 0.05 and 100 mg/kg body weight per 24 hours, preferably in amounts between 0.1 and 50 mg/kg, perhaps, in the form of several single doses to achieve desired results.

However, it may be necessary to deviate from the above dosage, depending on the nature and body weight of the patient, type and severity of the disease, preparation and application of the medicament concerned as well as on timing and intervals of application. There may be cases, for example, in which doses below those given above are sufficient, whereas in other cases the above quantities of active substance must be exceeded.

DETAILED DESCRIPTION OF THE PREFERRED EMBODIMENTS

While the following examples are mentioned for the purpose of explaining this invention in somewhat greater detail, they are not intended to restrict its scope.

EXAMPLES

EXAMPLE 1

4-methyl-2-hydroxy-caprophenone-oxime:

m-cresol and caproylchloride are converted in a wellknown mode to ester which, according to Fries, is rearranged to 4-methyl-2-hydroxy-caprophenone (P.P.T. Sah and H. H. Anderson, J. Am. Chem. Soc. 63, 3164 (1941). 20 g (0.1 Mol) of ketone, 10.6 g (0.15 Mol) of hydroxylamine hydrochloride, 35 ml of ethanol, and 7 ml water get added to them 19.5 g (0.5 Mol) sodium hydroxide along with stirring. The reactive mixture is heated five minutes with reflux cooling and allowed to cool down and is then added to an aqueous hydrochloric acid solution (55 ml of concentrated hydrochloric acid and 350 ml water). The resulting oxime is accommodated in ether and dried with anhydrous sodium sulphate. Ether is distilled off to obtain 21 g of crude product. Oxime with a flash point of 45° C. is then obtained, following recrystallisation from petrol ether.

EXAMPLE 2

5-methyl-2-hyroxy-caprophenone-oxime:

p-cresol and caproylchloride are converted in a wellknown mode to ester which, according to Fries, is rearranged to 5-methyl-2-hydroxy-caprophenone, 155° in b.p.$_{65}$ (cf. P.P.T. Sah and H. H. Anderson, J. Am. Chem. Soc. 63, 3164 (1941). 20 g (0.1 Mol) of ketone are solved in 45 ml ethanol and heated 30 minutes to boiling level under reflux cooling together with a concentrated aqueous solution of 7.5 g of hydroxylamine hydrochloride and 15 g of crystalline sodium acetate. Water is then added to the mixture, and the separated oxime recrystallised from ethanol/water, the flash point being between 83° C. and 85° C.

EXAMPLE 3

5-methyl-2-hydroxy-caprophenone-(N-phenyl-carbamoyl)-oxime:

2.2 g (0.01 Mol) of 5-methyl-2-hydroxy-caprophenone-oxime are dissolved in 25 ml of toluene and may be slightly heated in this process. Then 1.2 g (0.01 Mol) of phenylisocyanate are added, with the mixture being swirled. The mixture is allowed to stay for one hour, before the solvent is evaporated under vacuum conditions causing crystallisation of residue. Colourless crystals, between 117° C. and 120° C. in flash point, are obtained by recrystallisation from ethanol or ethanol/water.

EXAMPLE 4

5-methyl-2-hydroxy-laurophenone-oxime:

Ester, 28° C. in flash point, as formed from p-cresol and lauroyl chloride is converted in a well-known mode to ketone, between 42° C. and 43° C. in flash point, through rearrangement according to Fries. 29 g (0.1 Mol) of ketone is dissolved in an amount of ethanol just enough to produce a clear solution when an aqueous solution of 7 g of hydroxylamine hydrochloride and 15 g of crystalline sodium acetate is added. The latter solution is then heated 20 minutes along with reflux cooling. The oxime is separated from the reaction solution by cooling or adding of water. Colourless crystals, 93° C. in flash point, are obtained from ethanol.

EXAMPLE 5

3-chloro-2-hydroxy-caprophenone-oxime:

o-chloropheol and caproylchloride are converted in a wellknown mode to ester which with aluminium chloride, according to Fries, is rearranged by one-hour heating to 120° C. to 3-chloro-2-hydroxy-caprophenone, between 78° C. and 80° C. in flash point (ethanol/water, n-heptane). 22.6 g (0.1 Mol) of ketone are boiled three hours, along with reflux cooling, together with 15.2 (0.22 Mol) of hydroxylamine hydrochloride in 150 ml of absolute ethanol and 25 ml of pyridine. An oily residue is left, following evaporation of the solvent under vacuum conditions. The oxime, 102° C. to 103° C. in flash point, is obtained from treatment with ethanol/water and recrystallisation from n-heptane.

The following examples were accomplished in an analogous manner:

5-chloro-2-hydroxy-caprophenone-oxime, 100° C. in flash point (n-heptane);
3-chloro-2-hydroxy-laurophenone-oxime, 96° C. in flash point (ethanol);
5-chloro-2-hydroxy-laurophenone-oxime, 97° C. in flash point (ethanol).

EXAMPLE 6

4-pentoxy-2-hydroxy-acetophenone-oxime;

30.4 g (0.2 Mol) of 2,4-dihydroxyacetophenone were boiled 24 hours, along with reflux cooling, together with 45 g (0.3 Mol) of n- pentylbromide and 28 g of anhydrous calcium carbonate in 300 ml of dried acetone. The acetone was then evaporated under vacuum conditions. A small quantity of water was added to he residue and the latter shaken out with ether. Ketone, 33° C., in flash point, was obtained from the ethereal phase dried with anhydrous sodium sulphate, following removal of the ether. The reaction mixture of 11.1 g (0.05 Mol) of ketone, 7.5 g of potassium acetate, and 4.5 g of hydroxylamine hydrochloride was then heated three hours, along with reflux cooling, filtrated in hot condition, and water was added to the filtrate to get the oxime separated. 9 g of oxime, 66° C. to 67° C. in flash point, were obtained from n-heptane.

The following examples were obtained in an analogous manner:

4-butoxy-2-hydroxy-acetophenone-oxime, 87° C. in flash point (ethanol/water and n-heptane);
4-dodecyloxy-2-hydroxy-propiophenone-oxime, 63° C. in flash point (n-heptane);
4-hexadecyloxy-2-hydroxy-acetophenone-oxime, 86° C. to 87° C. in flash point (n-heptane);
4-octadecyloxy-2-hydroxy-acetophenone-oxime, 90° C. in flash point (ethanol).

EXAMPLE 7

4-decyloxy-2-hydroxy-acetophenone-oxime:

30.4 g (0.2 Mol) of 2,4-dihydroxyacetophenone were boiled 22 hours on water bath, along with reflux cooling, with 66.3 g (0.3 Mol) of n-decylbromide and 28 g of anhydrous potassium carbonate in 300 ml of dried acetone, before the acetone was allowed to evaporate in vacuum. The residue was accommodated in a small amount of water, extracted with ether, and the organic phase then separated was dried in anhydrous sodium sulphate. The ether was distilled off, and ketone, 35° C. in flash point, was obtained from the residue, following recrystallisation from ethanol. The reaction mixture of 14.6 g (0.05 Mol) of ketone and 7.6 g (0.11 Mol) of hydroxylamine hydrochloride was boiled three hours, along with reflux cooling, in 90 ml of absolute ethanol and 30 ml of pyridine. Evaporation of the solvents under vacuum conditions was followed by recrystallisation of the residue first from ethanol/water and then from n-heptane to give colourless crystals, 69° C. to 70° C. in flash point.

EXAMPLE 8

4-decyloxy-2-hydroxy-propiophenone-oxime:

16.6 g (0.1 Mol) of 2,4-dihydroxypropiophenone were heated for 20 hours, along with reflux cooling, together with 33.1 g (0.15 Mol) of decylbromide and 14 g of anhydrous potassium carbonate in 150 ml of dried acetone. The acetone was allowed to evaporate under vacuum conditions. The residue was accommodated in water, shaken out with ether, before the organic phase was dried in anhydrous sodium sulphate. Ketone, 30° C. in flash point, was obtained, after the ether had been distilled off. The reaction mixture of 9.2 g (0.03 Mol) of ketone in 15 ml of pyridine and 25 ml of absolute ethanol with 4.5 g (0.066 Mol) of hydroxylamine hydrochloride was boiled three hours, along with reflux cooling. Following evaporation of the solvents under vacuum conditions, the residue was washed in water and recrystallised from ethanol. Colourless crystals were obtained, with their flash point being 58° C. to 59° C.

EXAMPLE 9

4-benzyloxy-2-hydroxy-acetophenone-oxime:

30 g (0.2 Mol) of 2,4-dihyroxyacetophenone were dissolved in 300 ml of dried acetone. Then 28 g of anhydrous potassium carbonate were added, followed by addition of 38 g (0.3 Mol) of benzyl chloride. The mixture was heated about 20 hours, along with reflux cooling. Acetone was distilled off, and 2N H$_2$SO$_4$ was added to the residue. The solid ketone was drained off, treated with 2N KOH, and neutralised by washing in water. Colourless crystals, 103° C. to 105° C. in flash point, were obtained from ethanol and boiled three hours, along with reflux cooling, together with 12.8 g of hydroxylamine hydrochloride and 18.8 g of potassium acetate in 110 ml of ethanol. The compound given in the heading of this Example, 143° C. in flash point from ethanol/water was ultimately obtained when water had been added, following filtration of the reaction mixture.

EXAMPLE 10

4-butoxy-5-n-hexyl-2-2hydroxy-acetophenone-oxime:

A mixture of 7.1 g (0.03 Mol) of 2,4-dihyroxy-5-n-hexyl-acetophenone, 6.1 g (0.045 Mol) of n-butylbromide, and 4.2 g of anhydrous potassium carbonate was boiled in 50 ml of dried acetone on a water bath and along with reflux cooling for 20 hours, before the solvent was distilled off, the residue accommodated in water and shaken out with ether and the organic phase dried with anhydrous sodium sulphate. Ketone, 37° C. in flash point (n-heptane), was obtained, following separation of ether. 2.8 g (0.01 Mol) of ketone were boiled three hours, along with reflux cooling, in 30 ml of absolute ethanol and 6 ml of pyridine together with 1.52 g (0.022 Mol) of hydroxylamine hydrochloride. The solvent was distilled off and washed in water, before the residue was recrystallised from n-heptane. The flash point was 62° C.

EXAMPLE 11

4-pentoxy-2-hydroxy-caprophenone-oxime:

20.8 g (0.1 Mol) of 2,4-dihydroxycaprophenone were kept in a water bath at somewhere between 60° C. and 70° C. under reflux together with 22 g (0.145 Mol) of n-pentylbromide and 14 g of anhydrous potassium carbonate in 150 ml of dried acetone. The acetone was then evaporated under vacuum conditions, and water was added to the residue. Shaking-out with ether, drying of the organic phase with sodium sulphate, and removal of ether left a residue which solidified in the course of cooling. Ketone, 41° C. to 42° C. in flash point, was obtained by recrystallisation from ethanol. 14 g (0.05 Mol) of ketone were boiled three hours, along with reflux cooling, together with 7.6 g (0.11 Mol) of hydroxylamine hydrochloride and 15 g of potassium acetate in 200 ml of ethanol. The ethanol was distilled off, and about 100 ml of warm water were added. The oxime, left as insoluble residue from ethanol/water, was recrystallised to colourless crystals, 80° C. in flash point.

EXAMPLE 12

4-decyloxy-2-hydroxy-caprophenone-oxime:

20.8 g (0.1 Mol) of 2,4-dihydroxycaprophenone together with 32 g (0.145 Mol) of n-decylbromide and 14 g of anhydrous potassium carbonate in 150 ml of dried acetone, as in Example 11, were converted to ketone, between 45° C. and 47° C. in flash point, which, in absence of potassium acetate, reacted with hydroxylamine hydrochloride in ethanolic solution to oxime, 57° C. in flash point (ethanol/water).

EXAMPLE 13

4-octyloxy-2-hydroxy-laurophenone-oxime:

29.2 g (0.1 Mol) of 2,4-dihydroxylaurophenone together with 28 g (0.145 Mol) of n-octylbromide and 14 g of anhydrous potassium carbonate in 150 ml of dried acetone, as in Example 11, are converted to ketone, 56° C. to 57° C. in flash point (ethanol), and, subsequently, with hydroxylamine hydrochloride in the presence of potassium acetate in ethanolic solution, converted to oxime, between 60° C. and 63° C. in flash point (ethanol, n-heptane). The following example was obtained in the same way: 4-decyloxy-2-hydroxy-laurophenone-oxime, between 64° C. and 69° C. in flash point (n-heptane, ethanol).

EXAMPLE 14

4-cyclohexyloxy-2-hydroxy-propiophenone-oxime:

8.3 g (0.05 Mol) of 2,4-dihydroxypropiophenone are kept at boiling temperature for eight hours, along with reflux cooling, together with 12 g (0.07 Mol) of cyclohexylbromide and 7 g of anhydrous potassium carbonate in 50 ml of ethyl glycol. The reaction mixture is subsequently filtrated and, allowed to cool down, before 250 ml of water are added. The ketone thus obtained, following recrystallisation from ethanol, exhibits a flash point of 80° C. to 81° C. The ketone, with hydroxylamine hydrochloride and in the presence of potassium acetate in ethanolic solution, was then converted to oxime, between 65° C. and 69° C. in flash point (ethanol n-heptane).

EXAMPLE 15

Action of 5-methyl-2-hydroxy-laurophenone-oxime on carbachol-induced contraction of trachea isolated from guinea pig:

The compound was checked for anti-asthmatic activity by means of measuring methods well established and known from the literature (cf p. 5) but modified for the purpose of this invention, using a tracheal spiral isolated from guinea pig. Measurements were conducted in thermostat-controlled organ bath in isotonic condition, using a contraction gauge with lever-type sensor, measuring coil, and measuring amplifier (inductive measurement by means of high-frequency oscillating circuit). Air was used for gassing. The suspension solution was of the following composition: 39.46 g of sodium chloride, 2.2 g of potassium chloride, 6.07 g of tris, 1.0 g of calcium chloride, 9.9 g of glucose, 1.0 ml of saturated magnesium chloride solution, 43 ml 1N hydrochloric acid per 5 l, pH 7.4.

Spasm was induced by 3.9 $\mu$M of carbachol. Subsequent addition of the compound tested caused strong dilatation which was clearly detectable even at a concentration of 50 $\mu$M of active substance.

EXAMPLE 16

Action of 5-methyl-2-hydroxy-laurophenone-oxime on arachidonic acid-induced contraction of lung strip isolated from guinea pig:

The experimental arrangement for this test system was analogous to that described in Example 15, through lung strip isolated from guinea pig was the subject of testing. Contraction, in this test, was induced by rising concentrations of arachidonic acid (concentrated solution in ethanol, kept in $N_2$ atmosphere) and cumulatively measured.

10 $\mu$M of the above compound, referred to in this invention, caused a reduction by 70 percent in contractile response to 0.1 $\mu$M to 100 $\mu$M of arachidonic acid ("metactoid inhibition" according to "General Theory of Drug-Receptor Interactions" by F. G. van den Brink in "Kinetics of Drug Action" ed. by J. M. van Ronum, Springer Berlin, Heidelberg, New York, 1977, Chapter 4, pp. 169–254).

EXAMPLE 17

Action on allergen-induced bronchoconstriction in vivo of sensitised guinea pig ("allergic asthma of guinea pig"):

This test was applied to male guinea pigs, 30 to 35 days from sensitisation, using 330 mg of aluminium hydroxide and 33 $\mu$g of ovalbuminper one kilogram of body weight (fresh preparation in physiological sodium chloride solution).

(Method was modified according to P. Anderson, Brit. J. Pharmacol. 77, 301 (1982).) The animals were anaesthetised by intraperitoneal application of 1.3 g/kg body weight of urethane, while 2 mg/kg body weight of Pavulon ® were intravenously injected for muscular relaxation. Intravenous injection of 40 $\mu$g of ovalbumin triggered off the allergen-induced bronchoconstriction which developed to the full scale of anaphylactic shock in all control animals, within few seconds. The animals, tracheostomised and with venous catheters, were artificially ventilated at rhythmic negative pressure in a tank respirator (f=16 min$^{-1}$; inspiration:expiration=1:1). Gas flow(V), breathing volume ($V_T$), and ECG were checked in the course of pneumotachography. The animals had been pretreated by two intraperitoneal injections of finely crushed 5-methyl-2-hydroxylaurophenone-oxime, suspended in agar-agar. The doses of 10 mg/kg body weight were applied 90 and 60 minutes prior to the experiment.

Complete inhibition of the ovalbumin-induced asthma reaction was obtained from the substance in all probands. All controls, on the other hand, died in the wake of one single intravenous injection of 40 $\mu$g of ovalbumin, all of them in apnoeic condition, following protracted severest asthmatic reaction ("silence chest syndrome").

The pretreated animals even tolerated without reaction two additional successive injections of 40 $\mu$g/kg body of ovalbumin. Comparable anti-asthmatic, anti-allergic, and anti-anaphylactic effects on a whole-animal model have not even been known from modern anti-asthmatics, such as ketotifen and disodium-cromoglycate (C. Armour and D. M. Temple, Agents Action 12, 285 (1982)).

EXAMPLE 10

Action of 5-methyl-2-hydroxy-laurophenone-oxime on contraction of pulmonary artery isolated from rabbit due to exogenous application of arachidonic acid:

The experimental arrangement for this test system was identical with that described in Example 15.

Strips of pulmonary artery isolted from rabbit were the subjects of testing.

Contraction was induced in the presence of 10 $\mu$M of indomethacin (blocking of cyclo-oxygenase route of arachidonic acid conversion) by rising concentrations of arachidonic acid and cumulatively measured.

The contractile response to something between 0.1 and 100 $\mu$M of arachidonic acid was reduced by an order from 60 to 80 percent by 10 $\mu$M of 5-methyl-2-hydroxy-laurophenoneoxime ("metactoid inhibition" according to "General Theory of Drug-Receptor Interactions" by F. G. van den Brink in "Kinetics of Drug Action" ed. by I. M. van Rossum, Springer Berlin, Heidelberg, New York, 1977, Chapter 4, pp. 169–254).

EXAMPLE 19

Inhibition of carrageenin-induced oedema of rat's paw:

Carrageenin odemea has been used as a model system in the international literature in the context of phlogistic processes and has proved to be suitable for in-vivo testing of substances for anti-phlogistic activities. Testing is conducted by methods common in international practice /C.A. Winter, E. A. Risley and G. W. Nuss, Proc. Soc. Exp. Biol. Med. 111, 544 (1962)/. Ten rats received intraperitoneal injections of 50 mg/kg body weight of 5-methyl-2-hydroxy-laurophenone-oxime in parallel with 0.1 ml of 0.1-per-cent carrageenin solution (per animal). The development of paw oedema was measured in one-hour intervals, following application, and compared with manifestations in a control group. The following findings were recorded:

TABLE 2

| Inhibition of carrageenin-induced oedema by 5-methyl-2-hydroxy-laurophenone-oxime | |
|---|---|
| Time (hr) | Inhibition (percent) |
| 0.5 | 43+ |
| 1 | 47+ |
| 2 | 34+ |
| 3 | 34+ |
| 4 | 31 |

TABLE 2-continued

| Inhibition of carrageenin-induced oedema by 5-methyl-2-hydroxy-laurophenone-oxime ||
|---|---|
| Time (hr) | Inhibition (percent) |
| 5 | 29 |

+significant, with P < 0.05

EXAMPLE 20

Inhibition of activity of lipoxygenase from rabbit reticulocytes:

Lipoxygenase from rabbit reticulocytes was obtained in electrophoretically and immunologically pure form by means of the method described in the literature /S. M. Rapoport et al., Eur. J. Biochem. 96, 545 (1979)/. Lipoxygenase activity was determined at 25° C. by amperometric measurement of oxygen consumption by means of a Clark electrode in the following system: 0.1M potassium phosphate, pH 7.4, with 0.2-per-cent sodium cholate and 0.53 mM linoleic acid. The enzyme concentration was 25 mM in the sample for measurement. The substances submitted for testing were dissolved in methyl glycol (fresh distillation in vacuum) and pre-incubated ten minutes with the enzyme at measurement temperature and in the absence of sodium cholate and linoleic acid. The compounds were diluted to the effect that final concentrations of methyl glycol did not exceed the level of two per cent in the pre-incubation sample. No remarkable inhibition occurred to control samples under these conditions. Enzyme reaction was started by addition of sodium cholate and linoleic acid. The titration curve of inhibition and, consequently, the concentrations required for inhibition by the order of 50 per cent were determined by variation of active substance concentrations. For comparison, the compounds were tested also on commercial lipoxygenase-1 from soybean.

The compounds, referred to in this invention, proved to differ drastically from two modern anti-asthmatics, kertotifen and disodiumcromoglycate, of which even an ultimate concentration of 1 mM failed to have an effect on reticulocyte lipoxygenase.

TABLE 3

| Inhibition of lipoxygenases from rabbit reticulocytes and soybean ||||
|---|---|---|---|
| Compound | Ultimate concentration (mM) | Inhibition (percent) of lipoxygenase from reticulocytes ($I_{50}$-value, mM in parentheses) | soybean |
| 5-methyl-2-hydroxy-laurophenone-oxime | 1.0 | 100 (0.007) | 67 |
| 5-chloro-2-hydroxy-caprophenone-oxime | 1.0 | 90 (0.3) | 24 |
| 4-hexyloxy-2-hydroxy acetophenone-oxime | 1.0 | 100 (0.26) | 68 |
| 4-hexadecyloxy-2-hydroxy-acetophenone-oxime | 0.5 | 75 (0.5) | 38 |

EXAMPLE 21

Inhibition of thrombocyte aggregation induced by arachidonic acid or the platelet activation factor:

The compounds were tested for antithrombotic and thrombolytic activity in vitro on the authentic cell system of man. High-thrombocyte plasma was obtained from the blood of clinically healthy donors by 1000×g centrifugation. Thrombocyte aggregation was measured by means of an aggregometer on the basis of diffuse scatter of light or absorption of light by resulting cell aggregates. The high-thrombocyte plasma was pre-incubated with the active substances at 37° C. for three minutes. Thrombocyte aggregation was then triggered off by alternative addition of 0.8 mM of arachidonic acid or 1 μM of platelet activation factor (PAF acether). Samples were agitated at a rate of 800 rpm.

The result was either significant delay or total inhibition of thrombocyte aggregation, depending on active substance concentrations used.

A concentration of 40 μM of any of the compounds tested caused dissolution of cell aggregates which had been formed, in the first place, in all cases of aggregation due to PAF-acether. Identical effects were observed when aggregation had been induced by 16 μM of arachidonic acid in washed thrombocyte suspensions. This behaviour is likely to suggest that the lipoxygenase inhibitors tested blocked thrombocyte aggregation in the latter's irreversible phase and thus proved to be thrombolytically active.

For example, a concentration of 44 μM of 4-hexyloxy-2-hydroxy-acetophenone-oxime retarded aggregation by about two minutes, while 60 μM caused total inhibition. Similar results were obtained also from other compounds, according to this invention, as well as from well-known lipoxygenase inhibitors, such as 4-nitrocatechol.

It thus will be seen that there are provided pharmaceutical compositions which pharmacologically valuable properties, and procedures for their preparation and applicability, which attain the various objects of the invention, and which are well adapted for the conditions of practical use. As numerous alternatives within the scope of the present invention, besides those alternatives, equivalents, embodiments and variations mentioned supra., will occur to those skilled in the art, it will be understood that the invention extends fully to all such equivalents and the like, and is to be limited only by the scope of the appended claims, and functional and structural equivalents thereof.

We claim:

1. A method for treating a human or animal patient suffering from a disease which is alleviated by inhibiting lipoxygenase therein comprising administering to said patient a compound of the formula,

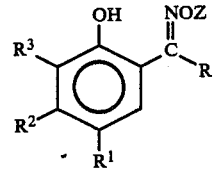

wherein
R is $C_1$–$C_{18}$ alkyl or aralkyl;
$R^1$ and $R^3$ are each hydrogen, $C_1$–$C_{12}$ alkyl, or chlorine;
$R^2$ is hydrogen, $C_1$–$C_{12}$ alkyl or $OR^4$, and $R^4$ is $C_1$–$C_{18}$ alkyl, $C_3$–$C_8$ cycloalkyl or aralkyl; and
Z is hydrogen, $C_1$–$C_{12}$ alkyl, $COR^5$, or $CONHR^5$, and $R^5$ is an aromatic or aliphatic residue, with the proviso that when
Z, $R^2$ and $R^3$ are each hydrogen, R is $C_7$–$C_{18}$ alkyl, in an amount effective to inhibit lipoxygenase.

2. The method of treating a human or animal patient according to claim 1, in which the compound is an oxime selected from the group consisting of
3-chloro-2-hydroxy-caprophenone-oxime,
5-chloro-2-hydroxy-caprophenone-oxime,
4-methyl-2-hydroxy-caprophenone-oxime,
5-methyl-2-hydroxy-caprophenone-(N-phenyl-carbamoyl)-oxime,
3-chloro-2-hydroxy-laurophenone-oxime,
5-chloro-2-hydroxy-laurophenone-oxime,
5-methyl-2-hydroxy-laurophenone-oxime,
4-n-butoxy-2-hydroxy-acetophenone-oxime,
4-n-pentoxy-2-hydroxy-acetophenone-oxime,
4-n-decyloxy-2-hydroxy-acetophenone-oxime,
4-n-hexadecyloxy-2-hydroxy-acetophenone-oxime,
4-n-octadecyloxy-2-hydroxy-acetophenone-oxime,
4-n-butoxy-5-n-hexyl-2-hydroxy-acetophenone-oxime,
4-benzyloxy-2-hydroxy-acetophenone-oxime,
4-n-decyloxy-2-hydroxy-propiophenone-oxime,
4-n-dodecyl-2-hydroxy.propiophenone-oxime,
4-cyclohexyl-2-hydroxy-propiophenone-oxime,
4-n-pentoxy-2-hydroxy-caprophenone-oxime,
4-n-decyloxy-2-hydroxy-caprophenonc-oxime,
4-n-octyloxy-2-hydroxy-laurophenone-oxime, and
4-n-decyloxy-2-hydroxy-laurophenone-oxime.

3. The method of claim 1 in which the compound of the formula is administered to said patient wherein when Z is hydrogen,
R is $C_7$–$C_{18}$ alkyl or aralkyl;
$R^1$ is hydrogen, $C_1$–$C_{12}$ alkyl, or chlorine;
$R^2$ and $R^3$ are hydrogen,
with the proviso that when Z, $R^2$ and $R^3$ are each hydrogen, R is $C_7$–$C_{18}$ alkyl, and when Z is $C_1$–$C_{12}$ alkyl, $COR^5$, or $CONHR^5$, and $R^5$ is an aromatic or aliphatic residue,
R is $C_1$–$C_{18}$ alkyl or aralkyl;
$R^1$ is hydrogen, $C_1$–$C_{12}$ alkyl, or chlorine;
$R^2$ is $C_1$–$C_{12}$ alkyl or $OR^4$, and $R^4$ is $C_1$–$C_{18}$ alkyl, $C_3$–$C_8$ cycloalkyl or aralkyl; and
$R^3$ is $C_1$–$C_{12}$ alkyl or chlorine.

4. The method of claim 1 in which the disease is bronchial asthma.

5. The method of claim 1 in which the disease is an allergy.

6. The method of claim 1 in which the disease is an inflammation.

7. The method of claim 1 in which the disease is thrombosis.

8. The method of claim 1 in which the disease is arteriosclerosis.

9. The method of claim 1 in which the disease is arterial hypertension.

10. The method of claim 1 in which the disease is a spastic condition of unstriated muscles of differentiated pathogenesis.

11. The method of claim 1 in which the compound 5-methyl-2-hydroxylaurophenoxime is administered to said patient.

12. A pharmaceutical composition useful for inhibiting lipoxygenase comprising, as an active component, a compound of the formula

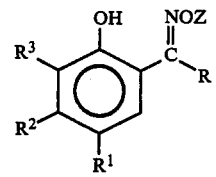

wherein
R is $C_1$–$C_{18}$ alkyl or aralkyl;
$R^1$ and $R^3$ are ech hydrogen, $C_1$–$C_{12}$ alkyl, or chlorine;
$R^2$ is hydrogen, $C_1$–$C_{12}$ alkyl or $OR^4$, and $R^4$ is $C_1$–$C_{18}$ alkyl, $C_3$–$C_8$ cycloalkyl or aralkyl; and
Z is hydrogen, $C_1$–$C_{12}$ alkyl, $COR^5$, or $CONHR^5$, and $R^5$ is an aromatic or aliphatic residue, with the proviso that when
Z, $R^2$ and $R^3$ are each hydrogen, R is $C_7$–$C_{18}$ alkyl, in an amount effective to inhibit lipoxygenase, in combination with a pharmaceutically acceptable carrier, wherein the composition is in unit dosage form.

13. The composition according to claim 12 in which the patient is treated with a compound of the formula wherein when Z is hydrogen,
R is $C_7$–$C_{18}$ alkyl or aralkyl;
$R^1$ is hydrogen, $C_1$–$C_{12}$ alkyl, or chlorine;
$R^2$ and $R^3$ are hydrogen, with the proviso that when Z, $R^2$ and $R^3$ are each hydrogen, R is $C_7$–$C_{18}$ alkyl, and when Z is $C_1$–$C_{12}$ alkyl, $COR^5$, or $CONHR^5$, and $R^5$ is an aromatic or aliphatic residue,
R is $C_1$–$C_{18}$ alkyl or aralkyl;
$R^1$ is hydrogen, $C_1$–$C_{12}$ alkyl, or chlorine;
$R^2$ is $C_1$–$C_{12}$ alkyl or $OR^4$, and $R^4$ is $C_1$–$C_{18}$ alkyl, $C_3$–$C_8$ cycloalkyl or aralkyl; and
$R^3$ is $C_1$–$C_{12}$ alkyl or chlorine.

14. The composition according to claim 12 in which the active component is a compound selected from the group consisting of
3-chloro-2-hydroxy-caprophenone-oxime,
5-chloro-2-hydroxy-caprophenone-oxime,
4-methyl-2-hydroxy-caprophenone-oxime,
5-methyl-2-hydroxy-carophenone-oxime,
5-methyl-2-hydroxy-caprophenone-(N-phenylcarbamoyl)-oxime,
3-chloro-2-hydroxy-laurophenone-oxime,
5-chloro-2-hydroxy-laurophenone-oxime,
5-methyl-2-hydroxy-laurophenone-oxime,
4-n-butoxy-2-hydroxy-acetophenone-oxime,
4-n-pentoxy-2-hydroxy-acetophenone-oxime,
4-n-decyloxy-2-hydroxy-acetophenone-oxime,
4-n-hexadecyloxy-2-hydroxy-acetophenone-oxime,
4-n-octadecyloxy-2-hydroxy-acetophenone-oxime,
4-benzyloxy-2-hydroxy-acetophenone-oxime,
4-n-decyloxy-2-hydroxy-propiophenone-oxime,
4-n-dodecyl-2-hydroxy-propiophenone-oxime,
4-cyclohexyl-2-hydroxy-propiophenone-oxime,
4-n-pentoxy-2-hydroxy-caprophenone-oxime,
4-n-decyloxy-2-hydroxy-caprophenone-oxime,
4-n-octyloxy-2-hydroxy-laurophenone-oxime, and
4-n-decyloxy-2-hydroxy-laurophenone-oxime.

15. The composition according to claim 13 in which the active component is 5-methyl-2-hydroxylaurophenoxime.

16. A pharmaceutical composition useful for inhibiting lipoxygenase comprising, as an active component, a compound of the formula $$\underset{R^1}{\underset{R^2}{R^3}}\underset{}{\overset{OH}{\bigcirc}}\overset{NOZ}{\underset{}{\overset{\|}{C}}}_R$$

wherein
   Z is hydrogen, $C_1$–$C_{12}$ alkyl, $COR^5$, or $CONH^5$, and $R^5$ is an aromatic or aliphatic residue;
   where Z is hydrogen,
      R is $C_7$–$C_{18}$ alkyl or aralkyl;
      $R^1$ is hydrogen, $C_1$–$C_{12}$ alkyl, or chlorine;
      $R^2$ and $R^3$ are each hydrogen, with the proviso that when Z, $R^2$ and $R^3$ are each hydrogen, R is $C_7$–$C_{18}$ alkyl, and when Z is $C_1$–$C_{12}$ alkyl, $COR^5$, or $CONHR^5$, and $R^5$ is an aromatic or aliphatic residue,
      R is $C_1$–$C_{18}$ alkyl or aralkyl;
      $R^1$ is hydrogen, $C_1$–$C_{12}$ alkyl, or chlorine;
      $R^2$ is $C_1$–$C_{12}$ alkyl or $OR^4$, and $R^4$ is $C_1$–$C_{18}$ alkyl, $C_3$–$C_8$ cycloalkyl or aralkyl; and
      $R^3$ is $C_1$–$C_{12}$ alkyl or chlorine
in an amount effective to inhibit lipoxygenase, in combination with a pharmaceutically acceptable carrier, wherein the composition is in aerosol form.

17. The composition according to claim 16 in which the active component is 5-methyl-2-hydroxylaurophenoxime.

18. A pharmaceutical composition useful for inhibiting lipoxygenase comprising, as an active component, a compound selected from the group consisting of
3-chloro-2-hydroxy-caprophenone-oxime,
5-chloro-2-hydroxy-caprophenone-oxime,
4-methyl-2-hydroxy-caprophenone-oxime,
5-methyl-2-hydroxy-caprophenone-oxime,
5-methyl-2-hydroxy-caprophenone-(N-phenylcarbamoyl)-oxime,
3-chloro-2-hydroxy-laurophenone-oxime,
5-chloro-2-hydroxy-laurophenone-oxime,
5-methyl-2-hydroxy-laurophenone-oxime,
4-n-butoxy-2-hydroxy-acetophenone-oxime,
4-n-pentoxy-2-hydroxy-acetophenone-oxime,
4-n-decyloxy-2-hydroxy-acetophenone-oxime,
4-n-hexadecyloxy-2-hydroxy-acetophenone-oxime,
4-n-octadecyloxy-2-hydroxy-acetophenone-oxime,
4-benzyloxy-2-hydroxy-acetophenone-oxime,
4-n-decyloxy-2-hydroxy-propiophenone-oxime,
4-n-dodecyl-2-hydroxy-propiophenone-oxime,
4-cyclohexyl-2-hydroxy-propiophenone-oxime,
4-n-pentoxy-2-hydroxy-caprophenone-oxime,
4-n-decyloxy-2-hydroxy-caprophenone-oxime,
4-n-octyloxy-2-hydroxy-laurophenone-oxime, and
4-n-decyloxy-2-hydroxy-laurophenone-oxime,
in an amount effective to inhibit lipoxygenase, in combination with a pharmaceutically acceptable carrier, wherein the composition is in aerosol form.

19. A pharmaceutical composition useful for inhibiting lipoxygenase comprising, as an active component, a compound of the formula $$\underset{R^1}{\underset{R^2}{R^3}}\underset{}{\overset{OH}{\bigcirc}}\overset{NOZ}{\underset{}{\overset{\|}{C}}}_R$$

wherein
   Z is $C_1$–$C_{12}$ alkyl, $COR^5$, or $CONHR^5$, and $R^5$ is an aromatic or aliphatic residue;
   R is $C_1$–$C_{18}$ alkyl or aralkyl;
   $R^1$ is hydrogen, $C_1$–$C_{12}$ alkyl, or chlorine;
   $R^2$ is $C_1$–$C_{12}$ alkyl or $OR^4$, and $R^4$ is $C_1$–$C_{18}$ alkyl, $C_3$–$C_8$ cycloalkyl or aralkyl; and
   $R^3$ is $C_1$–$C_{12}$ alkyl, or aralkyl
in an amount effective to inhibit lipoxygenase, in combination with a pharmaceutically acceptable carrier.

20. The pharmaceutical composition of claim 13, in which the active component comprises 0.1 to 99.5% by weight.

21. The pharmaceutical composition of claim 20, in which the active component comprises 0.5 to 90% by weight.

* * * * *